United States Patent
Wang et al.

(10) Patent No.: US 12,084,277 B2
(45) Date of Patent: *Sep. 10, 2024

(54) STERILIZATION AND DEODORIZATION WASTE BIN WITH DUAL-BAND ULTRAVIOLET TUBE

(71) Applicants: FUJIAN NASHIDA ELECTRONIC INCORPORATED COMPANY, Fujian (CN); NINE STARS GROUP(USA)INC

(72) Inventors: Shi ping Wang, Pingtan Fujian (CN); Jiang qun Chen, Pingtan Fujian (CN); You xi Luo, Pingtan Fujian (CN); Zhou Lin, Pingtan Fujian (CN)

(73) Assignees: FUJIAN NASHIDA ELECTRONIC INCORPORATED COMPANY, Fujian (CN); NINE STARS GROUP, (USA) INC, Ontario, CA (US)

(*) Notice: Subject to any disclaimer, the term of this patent is extended or adjusted under 35 U.S.C. 154(b) by 359 days.

This patent is subject to a terminal disclaimer.

(21) Appl. No.: 17/357,770

(22) Filed: Jun. 24, 2021

(65) Prior Publication Data
US 2022/0258968 A1   Aug. 18, 2022

(51) Int. Cl.
*A61L 2/10*   (2006.01)
*A61L 2/20*   (2006.01)
(Continued)

(52) U.S. Cl.
CPC ............... *B65F 7/00* (2013.01); *A61L 2/10* (2013.01); *A61L 2/202* (2013.01); *A61L 2/24* (2013.01);
(Continued)

(58) Field of Classification Search
CPC ... A61L 2/10; A61L 2/202; A61L 2/24; A61L 2202/11; A61L 2202/14; A61L 2202/15; A61L 2202/23
See application file for complete search history.

(56) References Cited

U.S. PATENT DOCUMENTS 5,337,581 A * 8/1994 Lott .................. A61L 11/00
422/292

* cited by examiner

*Primary Examiner* — Sean E Conley
(74) *Attorney, Agent, or Firm* — Raymond Y. Chan; David and Raymond Patent Firm

(57) ABSTRACT

The invention relates to a sterilization and deodorization waste bin, in particular to a sterilization and deodorization waste bin with a dual-band ultraviolet tube, which comprises an isolation cavity formed in an inner side of a lid and a dual-band ultraviolet tube mounted in the isolation cavity and capable of generating ultraviolet light waves for direct sterilization and ultraviolet light waves for ozone sterilization. The isolation cavity comprises a reflector and transparent quartz glass, an open surface of the reflector faces an inner cavity of the bin body, and the transparent quartz glass matches the open surface of the reflector in shape and size and covers an opening of the reflector through a silicone seal ring. The sterilization and deodorization waste bin with a dual-band ultraviolet tube has the following advantages: the operating environment of the ultraviolet tube is effectively improved, internal circuits and mechanical components outside of the isolation cavity are prevented from being affected, the service life is prolonged, and the use cost is reduced; the problems of light transmission and irradiation of the ultraviolet tube are solved, the ultraviolet light with the dual disinfection and sterilization function can sufficiently and effectively disinfect and sterilize the interior of the waste bin, so the disinfection and sterilization is effectively improved.

10 Claims, 8 Drawing Sheets

(51) Int. Cl.
    *A61L 2/24*         (2006.01)
    *B65F 1/02*         (2006.01)
    *B65F 1/16*         (2006.01)
    *B65F 7/00*         (2006.01)

(52) U.S. Cl.
    CPC ................ *B65F 1/02* (2013.01); *B65F 1/163* (2013.01); *B65F 1/1646* (2013.01); *A61L 2202/11* (2013.01); *A61L 2202/121* (2013.01); *A61L 2202/122* (2013.01); *A61L 2202/14* (2013.01); *A61L 2202/15* (2013.01); *A61L 2202/23* (2013.01); *B65F 2210/129* (2013.01); *B65F 2210/168* (2013.01)

STERILIZATION AND DEODORIZATION WASTE BIN WITH DUAL-BAND ULTRAVIOLET TUBE

BACKGROUND OF THE INVENTION

1. Technical Field

The invention relates to a sterilization and deodorization waste bin, in particular to a sterilization and deodorization waste bin with a dual-band ultraviolet tube. The invention is suitable for the waste bin with a cover.

2. Description of Related Art

Existing domestic waste bins are typically provided with a lid which can be opened with feet or by induction or touch. Waste in waste bins, particularly waste bins used in kitchens, may breed bacteria and give off foul smells which in turn pollutes the living environment of users, affects the olfactory sensation and health of the users, and causes potential sanitation hazards. To solve these problems, ultraviolet light waves are used for sterilization in the prior art, that is, a direct ultraviolet tube is disposed in the waste bins for sterilization of the internal environment of the waste bins. However, such solution has the following defects:

1. Ultraviolet rays emitted by the ultraviolet tube for direct sterilization can only be propagated linearly and cannot reach many positions when used for sterilization in the waste bin, which leads to some dead corners, and the sterilization effect is unsatisfying.

2. To ensure the light transmittance and the sterilization effect, the ultraviolet tube in the prior art is generally mounted in a naked manner, that is, the ultraviolet tube faces the interior of the waste bin in an uncovered manner, and the operating condition of the ultraviolet tube is directly affected by the severe environment in the waste bin, so that the service life of the ultraviolet tube is greatly shortened, the use cost is high, and popularization is difficult.

BRIEF SUMMARY OF THE INVENTION

In view of the defects of the prior art, the objective of the invention is to provide a sterilization and deodorization waste bin with a dual-band ultraviolet tube, which can avoid disinfection and sterilization dead corners, improve the disinfection and sterilization effect, improve the operating environment of the ultraviolet tube, prolong the service life of the ultraviolet tube, and reduce the use cost.

The objective of the invention is realized as follows:

A sterilization and deodorization waste bin with a dual-band ultraviolet tube comprises a bin body, a lid and a control circuit, and further comprises an isolation cavity formed in an inner side of the lid and a dual-band ultraviolet tube mounted in the isolation cavity, wherein the dual-band ultraviolet tube is capable of generating ultraviolet light waves for direct sterilization and ultraviolet light waves for ozone sterilization, the isolation cavity comprises a reflector and transparent quartz glass, an open surface of the reflector faces an inner cavity of the bin body, and the transparent quartz glass matches the open surface of the reflector in shape and size and covers an opening of the reflector through a silicone seal ring; and a control input terminal of a drive circuit of the dual-band ultraviolet tube is connected to a drive control terminal of the control circuit through a control switch.

Thus, the invention has the following key features:

1) The dual-band ultraviolet tube is sealed in the isolation cavity isolated from outside air by means of the reflector and the transparent quartz glass connected to the reflector in a sealing manner, only the glass needs to be cleaned when stained, and the dual-band ultraviolet tube in the isolation cavity will not be affected by the severe environment in the waste bin, the operating environment of the ultraviolet tube is optimized, the service life is prolonged, and the use cost is reduced.

2) The transparent quartz glass can improve the transmittance of ultraviolet light, and most other ultraviolet light waves in the isolation cavity can be reflected by the reflector onto the transparent quartz glass and penetrate through the glass to be irradiated into the waste bin, so that the intensity and quantity of effective waves are increased, and the problems of light transmission and irradiation of the ultraviolet tube are solved.

3) The dual-band ultraviolet tube can realize direct sterilization and ozone sterilization, ultraviolet light waves for direct sterilization have high photon energy and can penetrate through the cell membrane and cell nucleus of microorganisms to destroy the molecular bonds of DNA to disable the replication capacity or activity of the microorganisms and cause the death of the microorganisms, ultraviolet light waves for ozone sterilization can turn $O_2$ (oxygen) in air into $O_3$ ozone), which has a strong oxidation capacity and can be dispersed in the waste bin to effectively kill bacteria, and the dispersivity of the ozone exactly can make up for the defects of linear propagation and sterilization dead corners of the ultraviolet light, so the sterilization and deodorization function is enhanced, and these two type of ultraviolet light for disinfection and sterilization can sufficiently and effectively disinfect and sterilize the interior of the waste bin, so that the disinfection and sterilization effect is greatly improved. In addition, in the disinfection and oxidization process, redundant ozone will be combined into oxygen again within 30 min, so that ozone pollution is avoided.

4) The isolation cavity provides a good sterilization environment for ultraviolet light waves for ozone sterilization, and ozone with strong corrosivity can only disperse in the isolation cavity and the inner cavity of the bin body, so that circuit devices and mechanical components in the internal space of the lid will not be affected.

Further specifically:

The reflector is a plastic electroplated part, a resin cover having an inner side provided with a reflective film, or a stainless steel metal part having a reflective inner side.

The reflector is made of a material not prone to aging, or being corroded and oxidized, and thus will not be corroded by ozone, and the light wave reflection effect is improved.

The ultraviolet light waves for direct sterilization are 240-280 nm ultraviolet light waves and preferably 254 nm ultraviolet light waves for direct sterilization.

The ultraviolet light waves for direct sterilization are also called UVC, and ultraviolet light with a wavelength of 253.70-254 nm has the highest photon energy and the best disinfection and sterilization.

The ultraviolet light waves for ozone sterilization are 165-200 nm ultraviolet light waves and preferably 185 nm ultraviolet light waves for ozone sterilization.

The ultraviolet light waves for ozone sterilization (part of light waves of UVD) can turn $O_2$ (oxygen) in the air into $O_3$ (ozone) when irradiated into air, and the 185 nm ultraviolet light waves have a better ozone sterilization effect.

The section of the silicone seal ring is of an inverted U shape, and an edge of the transparent quartz glass is located in an inner cavity of the U shape to be completely wrapped in the silicone seal ring.

The isolation cavity formed below the lid may vibrate due to frequent opening and closing of the lid, and the transparent quartz glass may be broken due to vibrations; by wrapping the whole edge of the transparent quartz glass, breakage of the transparent quartz glass caused by vibrations can be reduced, and the structural reliability is guaranteed. In addition, the silicon can avoid aging caused by ultraviolet radiation.

The control switch is a Hall sensor, an angular sensor or a limit switch and comprises a control drive element and a measurement and control element separable from the control drive element, and the control drive element is connected to the dual-band ultraviolet tube and the control circuit.

For example, a control drive element of the angle sensor may be mounted on a main spindle of the lid; when the lid (or the lid plate when the lid consists of the lid plate and the circular housing) is opened by a certain angle (that is, the lid or the lid plate is opened), the control circuit receives a signal from the angle sensor to cut off power supplied to the ultraviolet tube to turn off the ultraviolet tube; when the lid (or the lid plate) is closed to a certain angle (the lid or the lid plate is closed), the ultraviolet tube is controlled to light up for disinfection and sterilization. For example, the Hall sensor comprises a Hall element used as the control drive element and a magnet used as the measurement and control element; when the magnet leaves the measurement range of the Hall element (that is, the lid or the lid plate is opened), the ultraviolet tube is turned off, when the magnet enters the measurement range of the Hall element (that is, the lid or the lid plate is closed), the ultraviolet tube is turned on. In this way, when the lid or the lid plate is opened, the control switch sends out a signal, the control circuit controls the dual-band ultraviolet tube to light off to protect the skin and eyes of users from being harmed by ultraviolet light; and when the lid or lid plate is closed, the control switch sends out a signal to enable the control circuit to turn on the ultraviolet tube to disinfect and sterilize the interior of the waste bin.

One side of the lid is hinged to the bin body, a box for storing the control circuit is disposed on one side of a hinge point of the lid, a groove is formed in the box, and the isolation cavity is located in the groove; and the control drive element and the measurement and control element of the control switch are mounted on the lid and the bin body, receptively.

When the lid cannot be separated from the bin body, the isolation cavity will turn upwards or downwards along with the lid, so the control switch is preferably mounted on a side edge or an open edge of the lid.

The lid comprises a circular housing and a lid plate, and one edge of the lid plate is hinged to the circular housing; the circular housing is disposed around the bin body, the control circuit is mounted in an inner cavity of the circular housing, and the isolation cavity is located in the groove formed in the circular housing; and two control switches are arranged, the control drive element and the measurement and control element of one control switch are mounted on the circular housing and the bin body, respectively, and the control drive element and the measurement and control element of the other control switch are mounted on the lid plate and the circular housing, respectively.

When the waste bin is used normal y; the control switch can be triggered when the lid is opened or closed; when the circular housing needs to be disassembled from the bin body, the control switches will be triggered, so that ultraviolet light is effectively prevented from leaking to protect human bodies against harm.

To sum up, according to the sterilization and deodorization waste bin with a dual-band ultraviolet tube provided by the invention, the dual-band ultraviolet tube is mounted in the isolation cavity provided with the reflector and the transparent quartz glass, so that the operating environment of the ultraviolet tube is effectively improved, internal circuits and mechanical components outside of the isolation cavity are prevented from being affected, the service life is prolonged, and the use cost is reduced; the problems of light transmission and irradiation of the ultraviolet tube are solved; the ultraviolet light with the dual disinfection and sterilization function can sufficiently and effectively disinfect and sterilize the interior of the waste bin, so that the disinfection and sterilization is effectively improved.

REFERENCE SIGNS

1, lid; 11, circular housing; 111, circular bin head; 112, circular middle seat; 12, lid plate; 13, control circuit; 131, Hall element; 132, magnet; 133, Hall element; 134, magnet; 14, lid opening and closing drive device; 2, bin body; 3, isolation cavity; 31, reflector; 32, transparent quartz glass; 321, silicone seal ring; 33, dual-band ultraviolet tube; 34, ultraviolet tube drive circuit.

The invention will be further described below in conjunction with the embodiments.

DETAILED DESCRIPTION OF THE INVENTION

Optimal Embodiment 1

Figure 1:
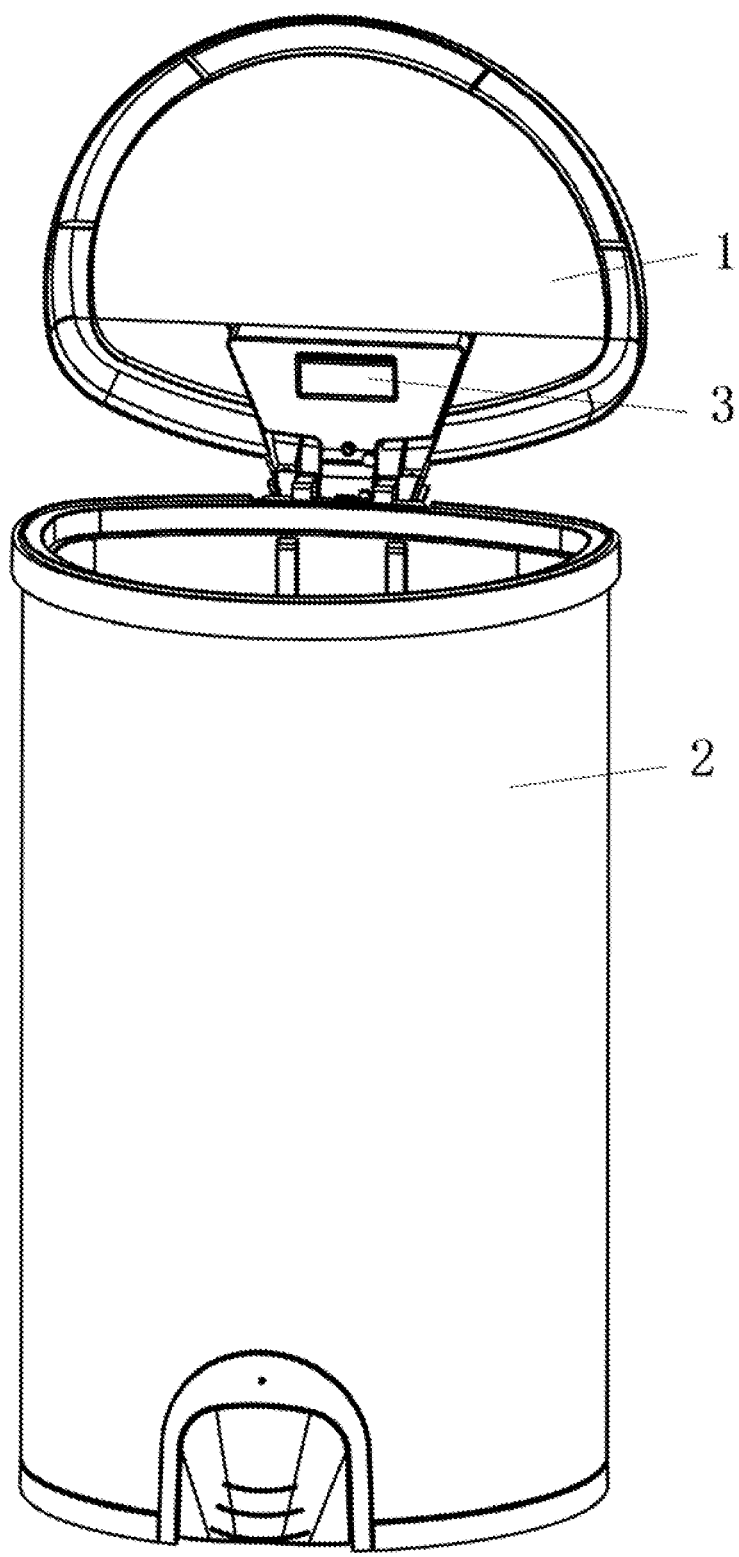
FIG. 1 is a structural view of a sterilization and deodorization waste bin with a dual-band ultraviolet tube in Embodiment 1 of the invention.
Figure 2:
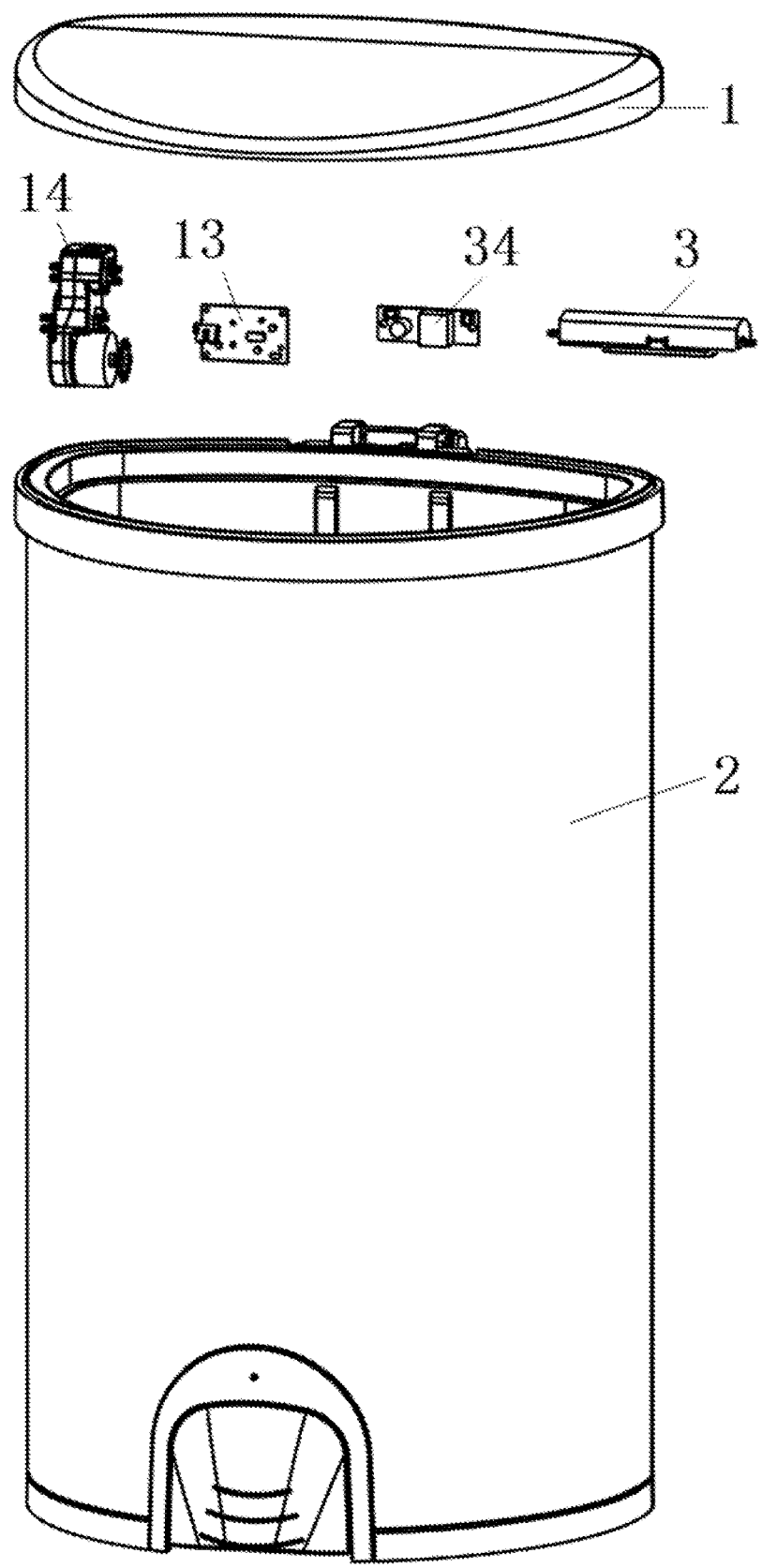
FIG. 2 is an exploded structural view of the sterilization and deodorization waste bin shown in FIG. 1.
Figure 3:
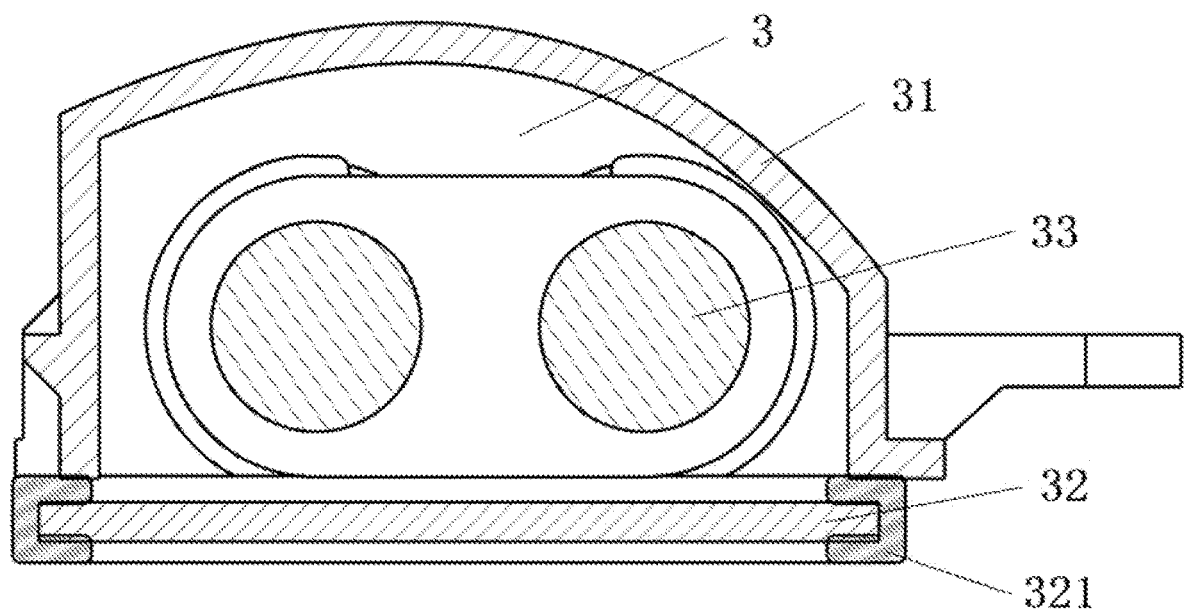
FIG. 3 is a structural view of an isolation cavity in the sterilization and deodorization waste bin with a dual-band ultraviolet tube.
Figure 4:
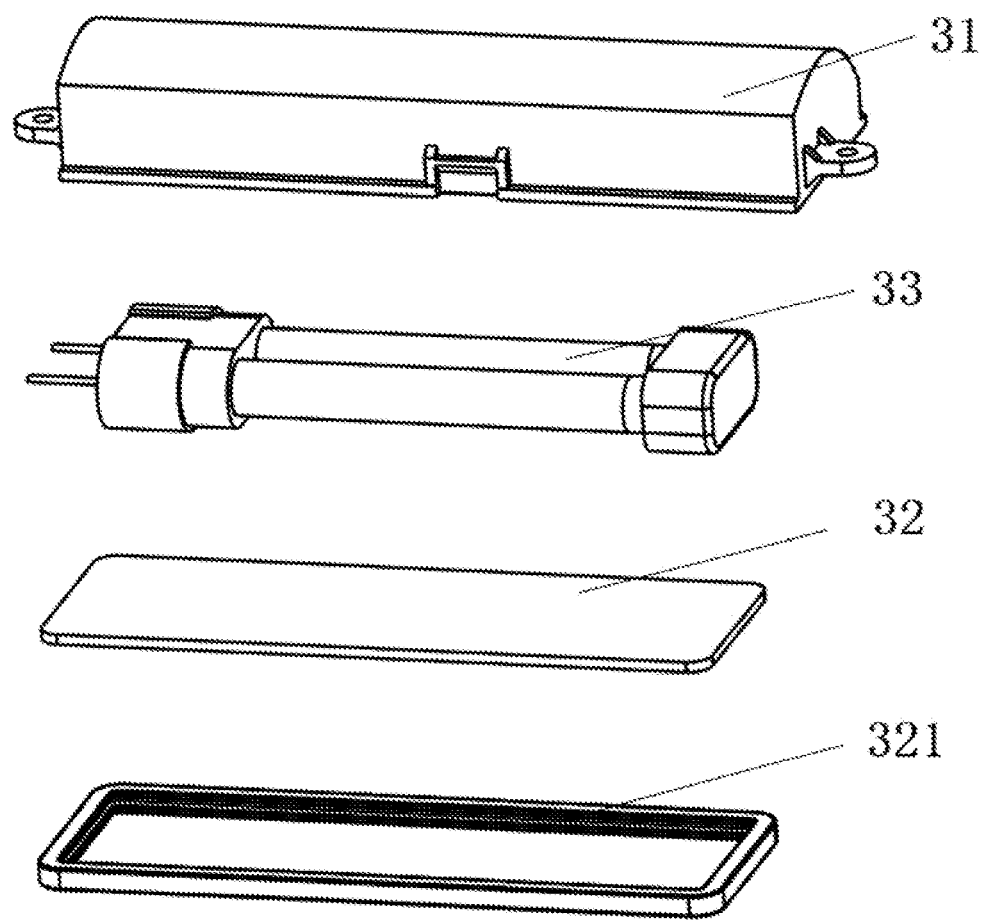
FIG. 4 is an exploded structural view of the isolation cavity.
Figure 5:
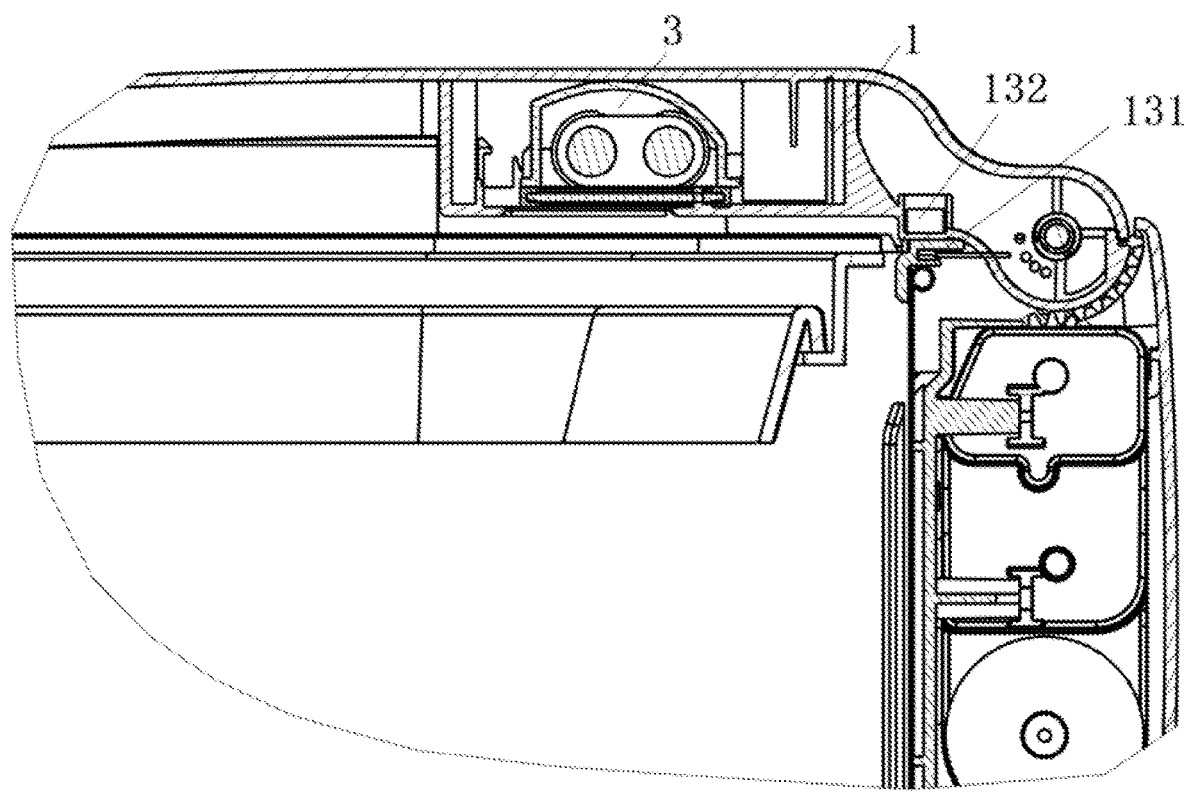
FIG. 5 is a sectional structural view of the sterilization and deodorization waste bin with a dual-band ultraviolet tube in Embodiment 1 of the invention.

This embodiment provides a sterilization and deodorization waste bin with a dual-band ultraviolet tube. In case where a lid of the waste bin cannot be separated from a bin body (for example, the waste bin is a foot-tread waste bin or a foot-touch waste bin, and in this embodiment, the waste bin is a foot-touch waste bin), foot-touch control and lid opening and closing belong to the prior art, and will no longer be detailed in Embodiment 1. Refer to FIG. 1-FIG. 5:

The sterilization and deodorization waste bin with a dual-band ultraviolet tube comprises a lid 1, a bin body 2 and a control circuit 13, wherein the bin body 2 is used for storing waste. The lid 1 is hinged to an opening in the top of the bin body 2, the control circuit 13 and a lid opening and closing drive device 14 are disposed on the bin body 2, an isolation cavity 3 isolated from air is formed below the lid 1, and a window pervious to light is disposed below the isolation cavity 3; considering the severe environment in the waste bin, a U-shaped dual band ultraviolet tube 33 is disposed in the isolation cavity 3 isolated front air; because of the low penetrability of ultraviolet light, the window pervious to light of the isolation cavity 3 needs to be made of transparent quartz glass 32 with extremely high light transmittance; the dual-band ultraviolet tube 33 generates ultraviolet light waves with a wavelength of 254 nm and ultraviolet light waves with a wavelength of 185 nm, ultraviolet light is irradiated into the waste bin through the window made of the quartz glass 32, and the ultraviolet light waves are used for sterilization and deodorization; wherein, the ultraviolet light waves with the wavelength of 254 nm (also called UVC) have high photon energy and can, when irradiated onto microorganisms, penetrate through the cell membrane and cell nucleus of the microorganisms to destroy the molecular bonds of DNA to disable the replication capacity or activity of the microorganisms and cause the death of the microorganisms; the ultraviolet light waves with the wavelength of 185 nm are irradiated in air to turn $O_2$ (oxygen) in the air into $O_3$ (ozone), which has a strong oxidation capacity and can effectively kill bacteria, and the dispersivity of the ozone exactly can make up the defects of linear propagation and sterilization dead corners of the ultraviolet light, so the sterilization and deodorization function is enhanced.

The isolation cavity 3 consists of a reflector 31, the transparent quartz glass 32 and a silicone seal ring 321, wherein the periphery of the transparent quartz glass 32 is fixed and protected by the U-shaped silicone seal ring 321, and the dual-band ultraviolet tube 33 is disposed in the airtight isolation cavity 3 formed by the reflector 3 and the transparent quartz glass 32. Because the ultraviolet light has a high aging capacity and the ozone has strong corrosivity, the dual-band ultraviolet tube 33 is disposed in the airtight isolation cavity 3, so that the ultraviolet light waves are prevented from being irradiated onto plastic structural members of a drive control mechanism and are concentrated onto waste in the waste bin, and the ozone generated by irradiation of the ultraviolet light waves will not be diffused into the internal space of the lid 1, which may otherwise corrode and oxidize the control circuit and internal structural components; in addition, the dual-band ultraviolet tube 33 is isolated and protected and thus will not be stained; if the window pervious to light is stained, only the transparent quartz glass 32 needs to be wiped, and sufficient ultraviolet light wave irradiation is guaranteed. The reflector 31 (the reflector 31 may be a plastic electroplated part, a reflective film, a stainless steel metal part, or a part made of other materials not prone to aging, corrosion and oxidization, and in this embodiment, the reflector 31 is a plastic electroplated part) can reflect ultraviolet light waves into the waste bin, so that the effective wave intensity is greatly increased. The ultraviolet light waves reflected by the reflector 31 can be irradiated into the waste bin only through the transparent quartz glass 32 which is pervious to most ultraviolet light waves with the wavelength of 254 nm and the wavelength of 185 nm, so that most ultraviolet light can be irradiated into the waste bin for sterilization and generate ozone in the waste bin for sterilization and deodorization. Because silicone has a high anti-aging capacity, the silicone seal ring 321 in this embodiment is made of seal silicone with a U-shaped section.

The lid 1 cannot be separated from the bin body 2, and a control switch is mounted on the bin body 2 (the control switch may be a Hall element, a limit switch, an angle sensor or the like, and in this embodiment, the control switch is a Hall element 131), a magnet 132 is mounted on the lid 1, and when the lid 1 is opened, the magnet 132 leaves the measurement range of the Hall element 131 along with the lid 1; after the control circuit 13 receives a signal from the Hall element 131, an ultraviolet tube drive circuit 34 controls the dual-band ultraviolet tube 33 to light off to stop generating ultraviolet light to protect the skin and eyes of users against harm. Only when the lid 1 is closed in place and the Hall element 131 detects that the magnet 132 is approaching, the control circuit 13 will control the dual-band ultraviolet tube 33 to light up, otherwise, the dual-band ultraviolet tube 33 will be kept off all the time.

Details that are not described in this embodiments belong to the prior art.

Optimal Embodiment 2

Figure 6:
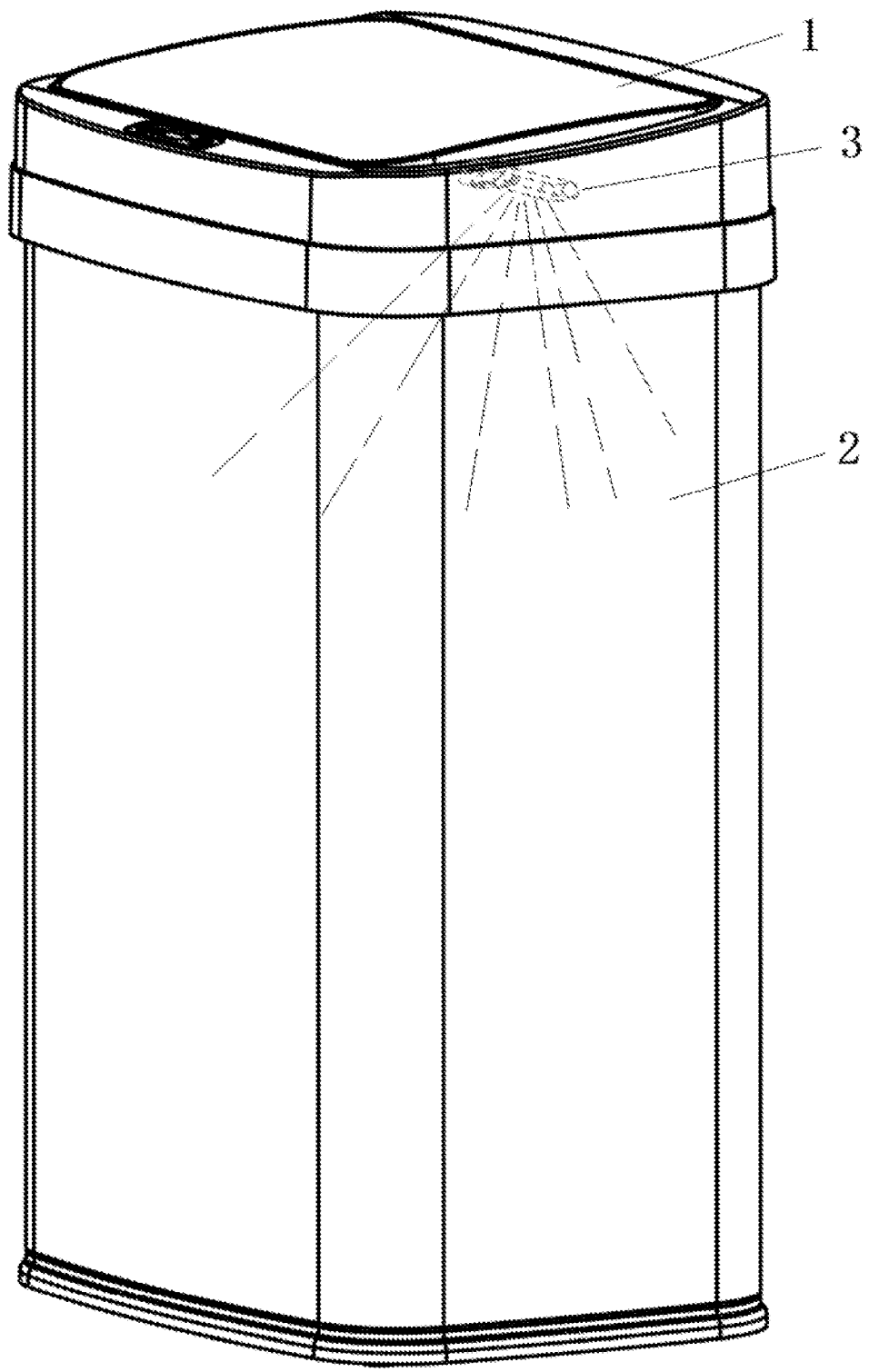
FIG. 6 is a structural view of a sterilization and deodorization waste bin with a dual-band ultraviolet tube in Embodiment 2 of the invention.
Figure 7:
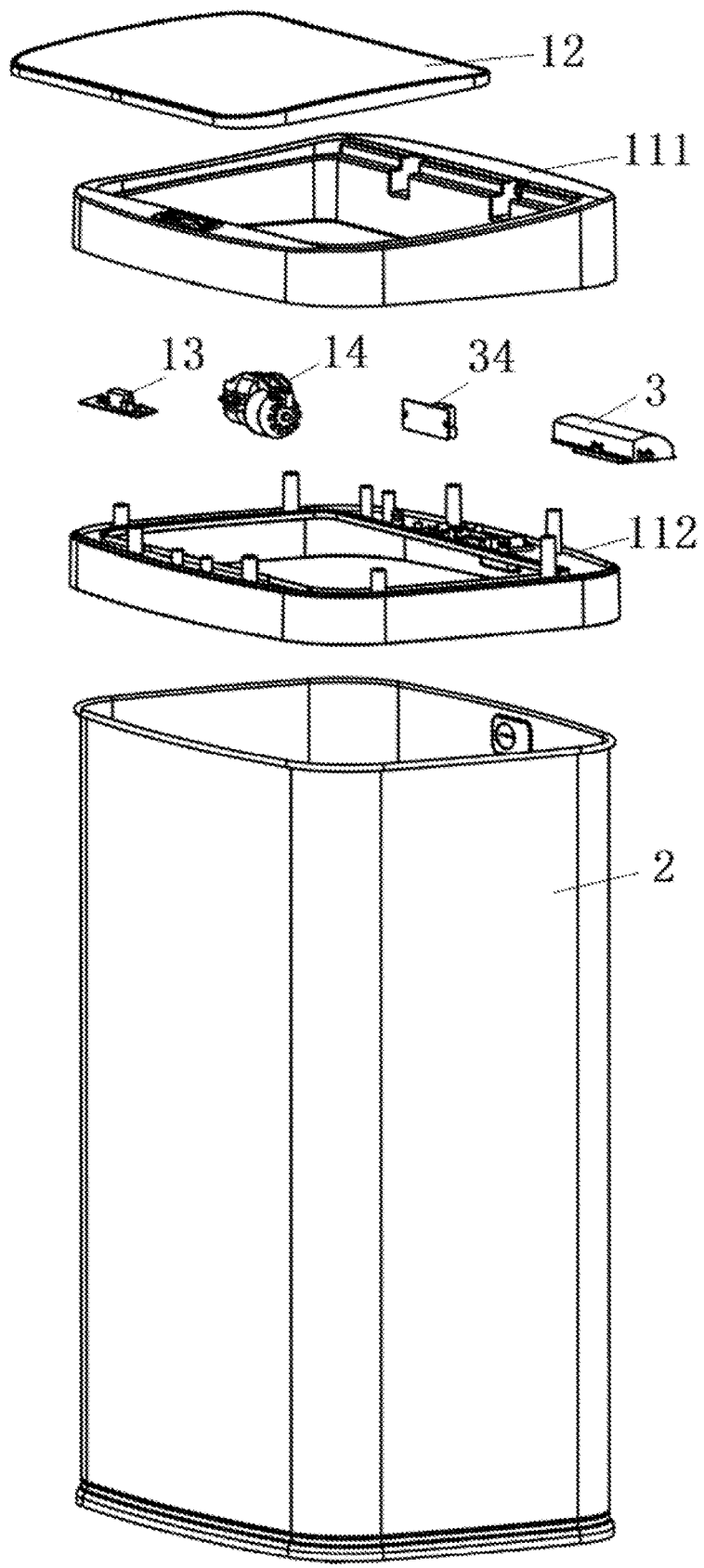
FIG. 7 is an exploded structural view of the sterilization and deodorization waste bin shown in FIG. 6.
Figure 8:
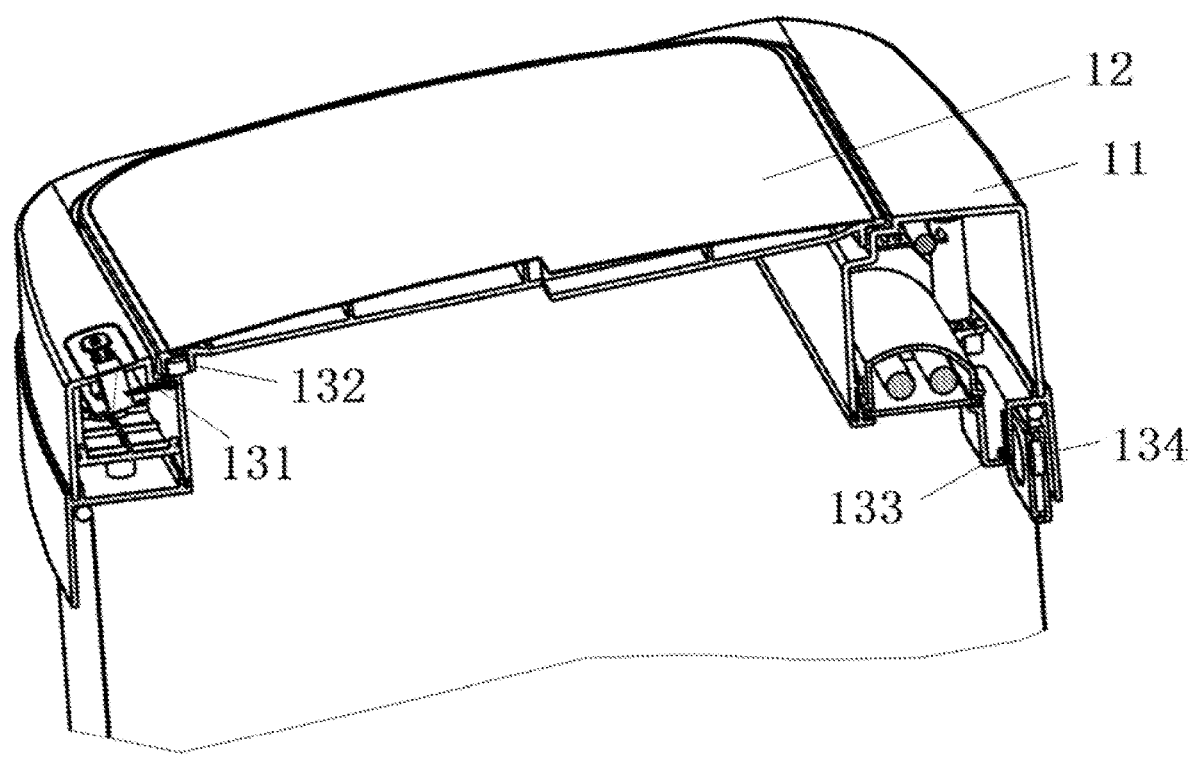
FIG. 8 is a sectional structural view of a lid of the sterilization and deodorization waste bin shown in FIG. 6.

This embodiment provides a sterilization and deodorization waste bin with a dual-band ultraviolet tube. In this embodiment, a lid of the waste bin can be separated from a bin body (such as an induction waste bin, and in this embodiment, the waste bin is an induction waste bin), an infrared induction part and lid opening and closing belong to the prior art, and will no longer be detailed in this embodiment. Referring to FIG. 3, FIG. 4, and FIG. 6-FIG. 8, the sterilization and deodorization baste bin with a dual-band ultraviolet tube comprises a lid 1, a bin body 2, and a control circuit 13, wherein the bin body 2 is used for storing waste. The lid 1 comprises a circular housing 11 (the circular cover 11 consists of a circular bin head 111 and a circular middle seat 122) and a lid plate 12, wherein the lid plate 12 is hinged to the circular housing 11, and they lid 1 is disposed at an opening in the top of the bin body 2. The control circuit 13 and a lid opening and closing drive device 14 are mounted in a cavity of the circular housing 11 formed after the circular bin head 111 and the circular middle seat 112 are buckled together, an isolation cavity 3 isolated from air is formed below the lid 1, a dual-band ultraviolet tube 33 is disposed in the isolation cavity 3, a window pervious to light is disposed below the isolation cavity 3 and is made of made of transparent quartz glass 32 with extremely high light transmittance, the dual-hand ultraviolet tube 33 generates ultraviolet light waves with a wavelength of 254 nm and ultraviolet light waves with a wavelength of 185 nm, ultraviolet light is irradiated into the waste bin through the window made of the quartz glass 32, and the ultraviolet light waves are used for sterilization and deodorization; wherein, the ultraviolet light waves with the wavelength of 185 nm generate ozone for sterilization and deodorization, and the ozone can be dispersed in the whole waste bin by means of its dispersivity to exactly make up the defects of linear propagation and sterilization dead corners of the ultraviolet light, so that the sterilization and deodorization function is enhanced.

The structure, material and effect of the isolation cavity 3, the reflector 31, the transparent quartz lass 32, the silicone seal ring 321 and the dual-band ultraviolet tube 33 and the sterilization and deodorization principle of the dual-band ultraviolet tube 33 can be understood with reference to the description in Embodiment 1, and will no longer be described in this embodiment.

The lid 1 can be separated from the bin body 2 and consists of the circular housing 11 and the lid plate 12, wherein a control switch is mounted on the bin body 2 (the control switch may be a Hall element, a limit switch, an angle sensor or the like, and in this embodiment, the control switch is a Hall element, namely Hall element 131 and Hall element 133), a magnet 134 is mounted on the bin body 2, and when the lid 1 is separated from the bin body 2, the magnet 134 leaves the measurement range of the Hall element 133; after the Hall element 133 generates a signal, the control circuit 13 controls the dual-band ultraviolet tube 33 to light off to stop generating ultraviolet light to protect the skin and eyes of users against harm. Similarly, a magnet 132 is mounted on the lid plate 12; when the lid plate 12 is opened, the magnet 132 leaves the measurement range of the Hall element 131 along with the lid plate 12; after the Hall element 131 generates a signal, the control circuit 13 controls the dual-band ultraviolet tube 33 to light off to stop generating ultraviolet light to protect the skin and eyes of users against harm. Only when the lid plate 12 is closed in plate and is placed on the bin body 2, the control circuit 13 will control the dual-band ultraviolet tube 33 to light up to work, otherwise, the control the dual-band ultraviolet tube 33 will be always in an off state. On this basis, the sterilization time of the ultraviolet tube can be set.

Details that are not described in this embodiments belong to the prior art.

The above embodiments are merely preferred ones of the invention, and are not intended to limit the invention. Any modifications, equivalent substitutions, and improvements made based on the spirit and principle of the invention should also fall within the protection scope of the patent.

What is claimed is:

1. A sterilization and deodorization waste bin, comprising a bin body, a lid, and a control circuit and further comprising an isolation cavity formed in an inner side of the lid and a dual-band ultraviolet tube mounted in the isolation cavity, wherein the dual-band ultraviolet tube is capable of generating ultraviolet light waves for direct sterilization and ultraviolet light waves for ozone sterilization, the isolation cavity comprises a reflector and transparent quartz glass, an open surface of the reflector faces an inner cavity of the bin body, and the transparent quartz glass matches the open surface of the reflector in shape and size and covers an opening of the reflector through a silicone seal ring, wherein a control input terminal of a drive circuit of the dual-band ultraviolet tube is connected to a drive control terminal of the control circuit through a control switch.

2. The sterilization and deodorization waste bin according to claim 1, wherein the reflector is selected from the group consisting of a plastic electroplated part, a resin cover having an inner side provided with a reflective film, and a stainless steel metal part having a reflective inner side.

3. The sterilization and deodorization waste bin according to claim 1, wherein the ultraviolet light waves for direct sterilization are 240-280 nm ultraviolet light waves for direct sterilization.

4. The sterilization and deodorization waste bin according to claim 1, wherein the ultraviolet light waves for ozone sterilization are 165-200 nm ultraviolet light waves for ozone sterilization.

5. The sterilization and deodorization waste bin according to claim 1, wherein a section of the silicone seal ring is of an inverted U shape, and an edge of the transparent quartz glass is located in an inner cavity of the section of the inverted U shape of the silicone seal ring to be completely wrapped in the silicone seal ring.

6. The sterilization and deodorization waste bin according to claim 1, wherein the control switch is selected from the group consisting of a Hall sensor, an angle sensor and a limit switch and comprises a control drive element and a measurement and control element separable from the control drive element, and the control drive element is connected to the control circuit.

7. The sterilization and deodorization waste bin according to claim 1, wherein a side of the lid is hinged to the bin body, a box for storing the control circuit is disposed on a side of a hinge point of the lid, a groove is formed in the box, and the isolation cavity is located in the groove, wherein the control switch comprises a control drive element and a measurement and control element, wherein the control drive element and the measurement and control element of the control switch are mounted on the lid and the bin body, respectively.

8. The sterilization and deodorization waste bin according to claim 1, further comprising another control switch, wherein the lid comprises a circular housing and a lid plate, and an edge of the lid plate is hinged to the circular housing, wherein the circular housing is disposed around the bin body, the control circuit is mounted in an inner cavity of the circular housing, and the isolation cavity is located in a groove formed in the circular housing, wherein each of the control switch and the another control switch comprises a control drive element and a measurement and control element, wherein the control drive element and the measurement and control element of the control switch are mounted on the circular housing and the bin body, respectively, wherein the control drive element and the measurement and control element of the another control switch are mounted on the lid plate and the circular housing, respectively.

9. The sterilization and deodorization waste bin according to claim 1, wherein the ultraviolet light waves for direct sterilization are 254 nm ultraviolet light waves for direct sterilization.

10. The sterilization and deodorization waste bin according to claim 1, wherein the ultraviolet light waves for ozone sterilization are 185 nm ultraviolet light waves for ozone sterilization.

* * * * *